(12) United States Patent
Lee

(10) Patent No.: US 7,601,970 B2
(45) Date of Patent: Oct. 13, 2009

(54) ALTERNATING CURRENT NEGATIVE ION AND SILVER ION GENERATOR

(75) Inventor: Cheong-Ho Lee, Seoul (KR)

(73) Assignee: CYMA World Co., Ltd, Yusung-Gu Daejeon (KR)

( * ) Notice: Subject to any disclaimer, the term of this patent is extended or adjusted under 35 U.S.C. 154(b) by 172 days.

(21) Appl. No.: 11/910,437

(22) PCT Filed: Jun. 17, 2005

(86) PCT No.: PCT/KR2005/001889
§ 371 (c)(1), (2), (4) Date: Oct. 1, 2007

(87) PCT Pub. No.: WO2006/112569
PCT Pub. Date: Oct. 26, 2006

(65) Prior Publication Data
US 2008/0191145 A1    Aug. 14, 2008

(30) Foreign Application Priority Data
Apr. 18, 2005    (KR)    ............... 10-2005-0031763

(51) Int. Cl.
*H01J 27/02* (2006.01)
(52) U.S. Cl. .................................. 250/423 R
(58) Field of Classification Search ............... 250/423 R
See application file for complete search history.

(56) References Cited

U.S. PATENT DOCUMENTS

| | | | |
|---|---|---|---|
| 5,147,297 A | * | 9/1992 | Myers et al. ............ 604/20 |
| 5,897,673 A | | 4/1999 | Nishida et al. |
| 6,752,970 B2 | | 6/2004 | Schwartz et al. |

FOREIGN PATENT DOCUMENTS

| | | |
|---|---|---|
| CN | 1375348 A | 10/2002 |
| JP | 11197230 | 7/1999 |
| KR | 2005-13665 | 2/2004 |
| KR | 2004-80321 | 9/2004 |
| WO | 2004054628 | 7/2004 |

* cited by examiner

*Primary Examiner*—Kiet T Nguyen
(74) *Attorney, Agent, or Firm*—Lexyoume IP Group, LLC.

(57) ABSTRACT

Disclosed herein is an AC negative ion and silver ion generator. The AC negative ion generator includes an AC power supply unit, an oscillation unit, a switching unit, a boosting unit, and an output unit. The AC power supply unit supplies an AC voltage required to operate the ion generator. The oscillation unit oscillates and generates an output pulse having a certain frequency when the voltage is supplied by the AC power supply unit. The switching unit performs a switching operation in response to an output frequency of the oscillation unit. The boosting unit boosts an AC voltage having a certain frequency, output through the switching unit, to a high AC voltage required to generate negative ions. The output unit transmits the high voltage to a discharge electrode placed at a negative ion generation unit. Accordingly, the AC negative ion generator can simultaneously generate negative ions and nano-sized silver ions in indoor air, prevent bad influence of the outflow of a high voltage on various electronic parts, convert polluted indoor air into clean, fresh and refreshing air, and perform antimicrobial and disinfecting actions on various airborne microbes, so that a comfortable and fresh indoor environment can always be maintained and the cleanliness of indoor air can be greatly improved, thus improving the metabolism of a human body.

1 Claim, 2 Drawing Sheets

ALTERNATING CURRENT NEGATIVE ION AND SILVER ION GENERATOR

BACKGROUND OF THE INVENTION

1. Field of the Invention

The present invention relates, in general, to an alternating current negative ion and silver ion generator and, more particularly, to an alternating current negative ion and silver ion generator, which simultaneously generates pure negative ions, lacking ozone and nitrogen oxide, and nano-sized silver ions, thereby converting polluted indoor air into clean, fresh and refreshing air, and which sterilizes various airborne microbes to maintain a comfortable and fresh indoor environment, thus greatly improving the cleanliness of indoor air and preventing the bad influence of polluted air on various electronic products.

2. Description of the Related Art

Generally, clean air in woods contains a lot of negative ions having negative charges, while waste gas exhausted from vehicles and smoke generated from factories contains a lot of positive ions having positive charges.

Further, the fact that, as a human body breathes a lot of negative ions, oxidized physical function is deoxidized and normal physical function is activated, has already been researched and reported to the academic community.

Further, recently, with rapid industrial development, air pollution is becoming serious. As a result, more and more positive ions are emitted, so that it is essential to generate negative ions and neutralize the positive ions. Accordingly, various negative ion generators for generating negative ions required to neutralize positive ions contained in indoor air have been developed and used indoors.

However, most conventional negative ion generators are constructed to supply a high voltage through a negative ion generation tip, thus locally generating negative ions using corona discharge or plasma discharge. Accordingly, as the conventional negative ion generators locally generate negative ions when they are used for a long period of time, harmful substances, such as ozone or nitrogen oxide, are generated, so that a user has a headache and feels nauseated and oppressed by the unpleasant smell, thus the user's health is greatly damaged.

Further, the conventional negative ion generators are constructed so that only a discharge electrode (a tip) exists, and are operated so that, if a negative (−) high voltage pulse is applied to the discharge electrode and electrons are generated in the air, the electrons cause oxygen itself to be negative while colliding with oxygen in the air. In particular, most conventional Direct Current (DC) negative ion generation modules are problematic in that, since a high voltage flows out from the modules, the modules continuously cause enormous damage to and bad influence on several electronic parts near the modules, thus increasing a risk of degrading electronic products.

Among the negative ion generation modules, an AC negative ion generation module, in particular, is problematic in that it uses illegal phase control, thus badly influencing other electronic products.

SUMMARY OF THE INVENTION

Accordingly, the present invention has been made keeping in mind the above problems occurring in the prior art, and an object of the present invention is to provide an AC negative ion and silver ion generator, which generates nano-sized silver ions together with negative ions, thereby converting polluted indoor air into clean, fresh and refreshing air without badly influencing various electronic products, and which performs antimicrobial and disinfecting actions on various airborne microbes, thus maintaining a comfortable and fresh indoor environment, greatly improving the cleanliness of indoor air, and consequently improving the metabolism of a human body.

In order to accomplish the above object, the present invention provides an Alternating Current (AC) negative ion and silver ion generator, comprising an AC power supply unit for supplying an AC voltage required to operate the ion generator; an oscillation unit including first and second resistors, first and second diodes and a first condenser, the oscillation unit oscillating and generating an output pulse having a certain frequency when the voltage is supplied by the AC power supply unit; a switching unit including third and fourth resistors and a Silicon Controlled Rectifier (SCR) to perform a switching operation in response to an output frequency of the oscillation unit; a boosting unit for boosting an AC voltage having a certain frequency, output through the switching unit, to a high AC voltage required to generate negative ions; and an output unit including a fifth resistor, a third diode and a second condenser to output the high voltage supplied by the boosting unit to a negative ion generation unit, wherein the negative ion generation unit is driven by the high voltage output from the output unit, and nano-sized silver ions are coated on a metallic fiber placed at an end of a discharge electrode such that the negative ion generation unit simultaneously emits negative ions and silver ions from the metallic fiber when the negative ion generation unit is driven by the high voltage output from the output unit.

Accordingly, the AC negative ion and silver ion generator of the present invention is advantageous in that it can simultaneously generate negative ions and nano-sized silver ions in indoor air, prevent the bad influence of the outflow of high voltage on various electronic parts, convert polluted indoor air into clean, fresh and refreshing air, and perform antimicrobial and disinfecting actions on various airborne microbes, so that a comfortable and fresh indoor environment can always be maintained and the cleanliness of indoor air can be greatly improved, thus improving the metabolism of a human body.

DESCRIPTION OF THE PREFERRED EMBODIMENTS

Hereinafter, embodiments of the present invention will be described in detail with reference to the attached drawings.

Figure 1:
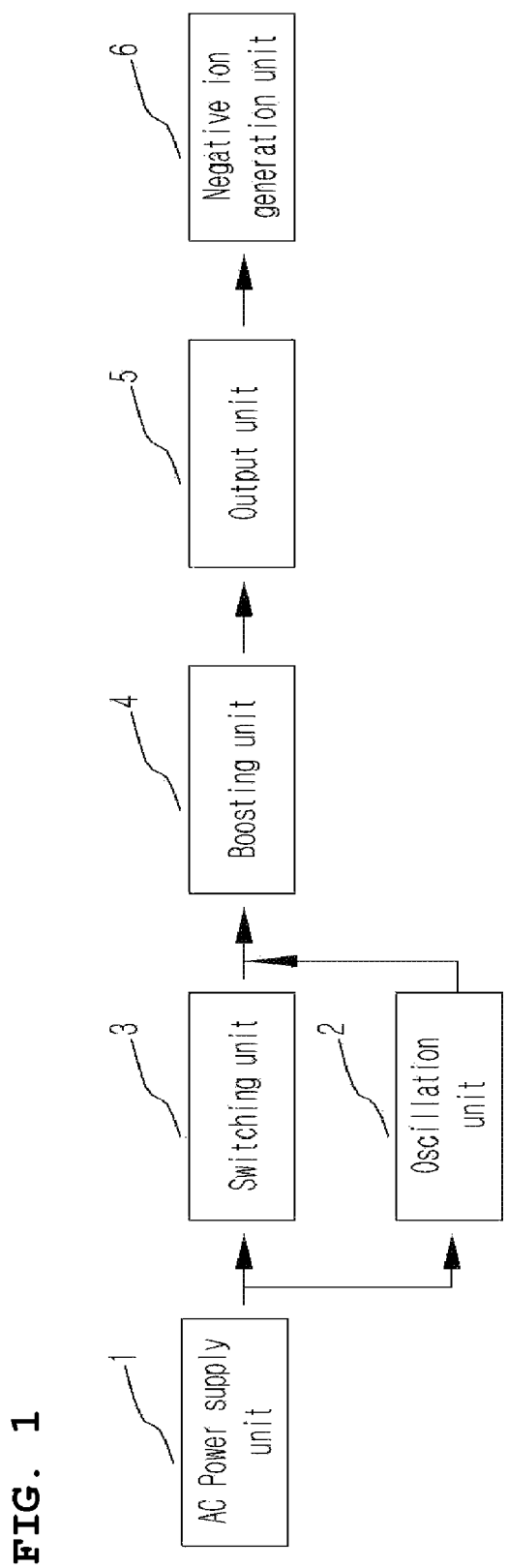
FIG. 1 is a block diagram of a negative ion and silver ion generator according to the present invention.
Figure 2:
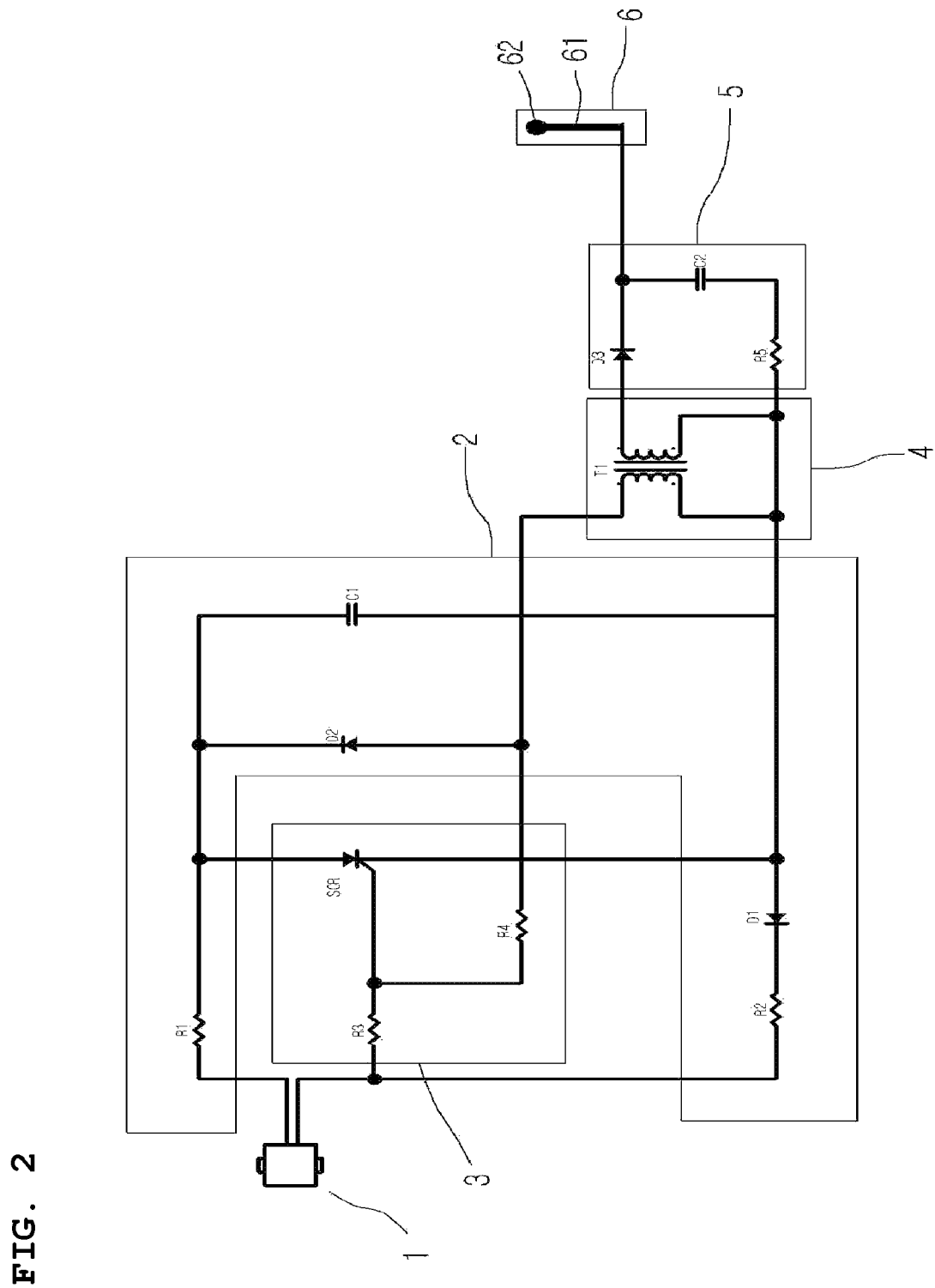
FIG. 2 is a detailed circuit diagram of the negative ion and silver ion generator according to the present invention.

FIG. 1 is a block diagram of a negative ion and silver ion generator according to the present invention, and FIG. 2 is a detailed circuit diagram of the negative ion and silver ion generator according to the present invention.

Referring to FIGS. 1 and 2, the AC negative ion and silver ion generator of the present invention includes an AC power supply unit 1, an oscillation unit 2, a switching unit 3, a boosting unit 4, and an output unit 5. The AC power supply unit 1 includes a power plug J1 and supplies AC voltage required to operate the AC negative ion generator.

The oscillation unit 2 includes resistors R1 and R2, diodes D1 and D2 and a condenser C1, and oscillates and generates an output pulse having a certain frequency when the voltage is supplied by the AC power supply unit 1.

The switching unit 3 includes resistors R3 and R4 and a Silicon Controlled Rectifier (SCR) and performs a switching operation in response to the output frequency of the oscillation unit 2.

The boosting unit 4 boosts the AC voltage having a certain frequency, output through the switching unit 3, to a high AC voltage required to generate negative ions.

The output unit 5 includes a resistor R5, a diode D3 and a condenser C2 and operates to transmit the high voltage provided by the boosting unit 4 to a discharge electrode 61 placed at a negative ion generation unit 6, thus causing negative ions and nano-sized silver ions to be emitted from a bundle of metallic fibers 62 placed at an end of the discharge electrode 61 while the bundle of metallic fibers 62 is coated with negative ions.

The operation and effect of the AC negative ion and silver ion generator of the present invention having the above construction is described in detail.

First, the power plug J1 of the AC power supply unit 1 is a generally well-known plug for commercial AC voltage, such as 220V, 100V or 120V, and is inserted into an outlet (not shown).

Further, the oscillation unit 2, including the resistors R1 and R2, the diodes D1 and D2 and the condenser C1, and the switching unit 3, including the resistors R3 and R4 and the SCR, are arranged in parallel with each other between the AC power supply unit 1 and the boosting unit 4, so that they organically interact with each other.

That is, if a source voltage is supplied through the AC power supply unit 1, the oscillation unit 2 oscillates according to the time constant determined by the resistance values of the resistors R1 and R2 and the capacitance value of the condenser C1, and thus generates an output pulse having a certain frequency. Further, the switching unit 3 performs a switching operation in response to the output frequency of the oscillation unit 2 and thus supplies an AC voltage having a certain frequency to the boosting unit 4, implemented with a high voltage transformer T1.

The resistor R1 performs the functions of protecting the diode D2 from a high voltage, applying a voltage, which causes a minimum current required to operate the SCR to flow through the anode of the SCR, to the SCR so as to prevent damage to the SCR, and dividing voltage at the anode of the SCR when the voltage is applied to the resistor R2 through the diode D1.

Further, the resistor R2 of the switching unit 3 decreases voltage at the cathode of the SCR and minimizes current consumption, at the same time that the resistor R2 protects the SCR and the diode D1 from overcurrent while passing a minimum current therethrough. Moreover, the resistor R2 protects the high voltage transformer T1 of the boosting unit 4.

Further, the resistors R3 and R4 of the switching unit 3 perform the function of dividing a bias voltage applied to the gate of the SCR, so that the resistors R3 and R4 interact with each other and apply a minimum bias voltage required to operate the SCR to the gate of the SCR.

Of course, the SCR performs a switching operation in response to the oscillation frequency determined by the resistors R1 and R2 and the condenser C1, and supplies a predetermined AC voltage (for example, 220V) to the boosting unit 4.

Meanwhile, the diode D1 divides a voltage applied to the resistors R3 and R4 and generates the gate voltage of the SCR at the same time that the diode D1 bypasses the output voltage of the SCR, thus providing an environment in which the SCR can be operated.

Further, the diode D2 of the oscillation unit 2 is connected in parallel with the SCR and the condenser C1 between the anode and cathode of the SCR and between both ends of the condenser C1. During the operation of the SCR, the diode D2 repeatedly performs the operation of blocking a reverse voltage, charging the condenser C1 using the AC voltage passed from the SCR through the primary coil of the high voltage transformer T1, and discharging the voltage charged in the condenser C1 to the SCR.

Further, during the operation of the SCR, the condenser C1 is charged through the high voltage transformer T1 and then discharged through the diode D2, thus allowing the SCR to perform a switching operation at a desired frequency.

Meanwhile, the boosting unit 4 is implemented with the high voltage transformer T1, which boosts an AC voltage of 220V, 100V or 120V, input through the SCR, to a voltage of about 6 KV, which is sufficient to ionize and emit silver molecules with which the bundle of metallic fibers 62 of the discharge electrode 61 placed at the negative ion generation unit 6 is coated.

Further, the diode D3 of the output unit 5 half-wave rectifies the high AC voltage output from the boosting unit 4. The condenser C2 filters out an AC component generated at the time of outputting the high voltage and passes only a voltage having a DC component therethrough, thus minimizing a risk of an electric shock occurring due to AC current. The resistor R5 limits current at the time of outputting the high voltage, thus minimizing a risk of an electric shock or electric leakage and preventing the occurrence of a fire, etc.

As described above, the voltage that is output from the output unit 5 and is transmitted to the discharge electrode 61 of the negative ion generation unit 6 is a negative (−) voltage, and a final output is a negative (−) high voltage.

Generally, a voltage for breaking down the insulation resistance of the atmosphere (air) using a high voltage is about 4 KV, so that the present invention is intended to generate a high voltage of about −6 KV using the boosting unit 4. Typically, as voltage becomes high, the insulation resistance of air is more easily broken down.

In this way, a negative high voltage of about −6 KV, output from the boosting unit 4, is supplied to the bundle of metallic fibers 62 through the discharge electrode 61 of the negative ion generation unit 6 and discharged to the air through the bundle of metallic fibers 62, so that a lot of negative ions and silver ions are generated by the breakdown of the insulation resistance of air.

That is, the output unit 5 of the present invention discharges a high voltage of about −6 KV to the air through the bundle of metallic fibers 62 of the discharge electrode 61 in the negative ion generation unit 6, that is a cathode, unlike the conventional corona discharge or plasma discharge, thus preventing the generation of harmful substances, such as ozone or nitrogen oxide.

In other words, since the bundle of metallic fibers 62 placed at the end of the discharge electrode 61 is coated with nano-sized silver ions, negative ions and silver ions are simultaneously emitted in the form of nano-sized particles from the bundle of metallic fibers 62 placed at the end of the discharge electrode 61 if a high DC voltage is applied to the discharge electrode 61 by the output unit 5 as described above.

The operating relations and principles of the negative ion generation unit 6 used in the present invention having the above construction are described in detail below.

First, the negative ion generation unit 6 is based on new types of physical principles related to the generation of negative ions at atmospheric pressure. The movement of free electrons in a conductor is limited by the external surface of the conductor and acts as a potential source of the electrons.

Electrons deviating from a power source can be generated by the tunneling of electrons at the bundle of micro metallic fibers 62 of the discharge electrode 61, which is coated with nano silver, using a high strength electromagnetic field. The high strength electromagnetic field is mostly formed due to the asymmetric plane of an electrode. A high voltage is applied through the output unit 5 so that the high strength electromagnetic field causes an electric field on the surface of the bundle of the negative metallic fibers 62.

The negative ion generation unit 6 applied to the present invention is designed so that a ramp basically emits negative ions similar to the prior art, and the bundle of nano silver-coated metallic fibers 62, having a small sectional area charged by a negative high voltage and having a greatly large surface area, emits silver ions (Ag+).

Such a negative high voltage causes an excess electron phenomenon at a cathode, and the excess electron phenomenon causes enticed air molecules to remove electrons, so that antimicrobial and disinfecting actions of nano silver are additionally performed without generating ozone or nitrogen oxide, which are harmful to the human body, thus clearing and refreshing air.

Various usages of the antimicrobial and disinfecting effects of silver are possible due to the development of nanotechnology, as described above.

In this case, nanotechnology, which is the technology of manipulating and processing a material on a molecular size scale of nanometers, divides silver into nano-sized particles and uniformly distributes the nano-sized particles to the material, so that a contact area between the silver particles and microorganisms is maximized, thus obtaining a sufficient disinfecting effect.

Two descriptions are possible with respect to the antimicrobial and disinfecting actions. One is because an electrical load, easily emitted as the silver ion (Ag+) while silver particles come into contact with moisture, eliminates the generative function of disease-causing microbes. The other is because active oxygen having a strong oxidization action is emitted while metal silver (Ag) combines with oxygen molecules ($O_2$), so that germicidal power is strengthened in proportion to the oxidization action.

Such nano-sized silver particles (average size: 10 to 40 nm) are attached to the bundle of metallic fibers using an inorganic binder through a coating-drying-firing procedure. In particular, the metallic fibers 62 used in this procedure are microfibers each having a fine thickness of 8 μm, and are metallic fibers (austenite-type metallic fiber having 0.08% carbon) that has excellent corrosion resistance, heat resistance and mechanical strength and has chemical uniformity and stability and uniform organization.

Meanwhile, a procedure of causing electrons accelerated by a high voltage to collide with neutral molecules and ionizing the neutral molecules is continuously performed so as to artificially generate negative ions. In this case, there is a problem in that ozone and nitrogen oxide are generated together as the by-product of the generated negative ions.

However, in the present invention, even though the voltage applied to the bundle of metallic fibers 62 that is placed at the discharge electrode 61 of the negative ion generation unit 6 is a high voltage, a pulse having a small amount of energy is applied, so that local fracture does not occur in a space adjacent to the discharge electrode, but the negative ion generation unit 6 causes electrons to tunnel the bundle of micro metallic fibers 62 coated with nano silver on the discharge electrode 61 while functioning as a potential source.

Therefore, not only are ozone and nitrogen oxide not formed in the generated negative ions, but also the antimicrobial and disinfecting actions, which are the properties of nano silver, are added, so that various airborne pollutants, microbes, pollen, mold, dust, etc. are neutralized and eliminated, thus clearing and refreshing air.

Further, the outflow of a high voltage can be prevented, so that damage to and bad influence on various electronic parts near the ion generator can be prevented.

As described above, the present invention provides a negative ion generator, which simultaneously generates negative ions and nano-sized silver ions through a bundle of metallic fibers of a negative ion generation unit, prevents a high voltage flowing out from the ion generator from badly influencing various electronic products, converts polluted indoor air into clean, fresh and refreshing air, and performs antimicrobial and disinfecting actions on various airborne microbes, so that a comfortable and fresh indoor environment can always be maintained and the cleanliness of indoor air can be greatly improved, thus improving the metabolism of a human body.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An Alternating Current (AC) negative ion and silver ion generator, comprising:
    an AC power supply unit for supplying an AC voltage required to operate the ion generator;
    an oscillation unit including first and second resistors, first and second diodes and a first condenser, the oscillation unit oscillating and generating an output pulse having a certain frequency when the voltage is supplied by the AC power supply unit;
    a switching unit including third and fourth resistors and a Silicon Controlled Rectifier (SCR) to perform a switching operation in response to an output frequency of the oscillation unit;
    a boosting unit for boosting an AC voltage having a certain frequency, output through the switching unit, to a high AC voltage required to generate negative ions; and
    an output unit including a fifth resistor, a third diode and a second condenser to output the high voltage supplied by the boosting unit to a negative ion generation unit,
    wherein the negative ion generation unit is driven by the high voltage output from the output unit, and nano-sized silver ions are coated on a metallic fiber placed at an end of a discharge electrode such that the negative ion generation unit simultaneously emits negative ions and silver ions from the metallic fiber when the negative ion generation unit is driven by the high voltage output from the output unit.

* * * * *